United States Patent
Harrison et al.

(10) Patent No.: US 10,493,041 B2
(45) Date of Patent: *Dec. 3, 2019

(54) OXYGEN-GENERATING COMPOSITIONS FOR ENHANCING CELL AND TISSUE SURVIVAL IN VIVO

(71) Applicant: WAKE FOREST UNIVERSITY HEALTH SCIENCES, Winston-Salem, NC (US)

(72) Inventors: Benjamin C. Harrison, Tobaccoville, NC (US); James J. Yoo, Winston-Salem, NC (US); Anthony Atala, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/142,480

(22) Filed: Sep. 26, 2018

(65) Prior Publication Data

US 2019/0022021 A1 Jan. 24, 2019

Related U.S. Application Data

(63) Continuation of application No. 12/532,520, filed as application No. PCT/US2008/004502 on Apr. 8, 2008.

(60) Provisional application No. 60/910,686, filed on Apr. 9, 2007.

(51) Int. Cl.
| | |
|---|---|
| *A61K 9/70* | (2006.01) |
| *A61K 31/77* | (2006.01) |
| *A61L 15/18* | (2006.01) |
| *A61L 15/26* | (2006.01) |
| *A61L 15/64* | (2006.01) |
| *A61L 26/00* | (2006.01) |
| *A61L 27/44* | (2006.01) |
| *A61L 27/58* | (2006.01) |
| *A61K 38/00* | (2006.01) |

(52) U.S. Cl.
CPC ............ *A61K 9/7007* (2013.01); *A61K 31/77* (2013.01); *A61L 15/18* (2013.01); *A61L 15/26* (2013.01); *A61L 15/64* (2013.01); *A61L 26/009* (2013.01); *A61L 26/0076* (2013.01); *A61L 27/446* (2013.01); *A61L 27/58* (2013.01); *A61K 38/00* (2013.01)

(58) Field of Classification Search
CPC ...... A61K 9/7007; A61K 31/77; A61K 38/00; A61L 15/18; A61L 15/26; A61L 15/64; A61L 26/0076; A61L 26/009; A61L 27/446; A61L 27/58; C08L 67/04
See application file for complete search history.

(56) References Cited

U.S. PATENT DOCUMENTS

| | | | |
|---|---|---|---|
| 3,839,220 A | 10/1974 | Barchas | |
| 3,977,988 A | 8/1976 | Tokiwa et al. | |
| 3,996,141 A | 12/1976 | Updike | |
| 4,411,872 A | 10/1983 | Bramson | |
| 4,507,285 A | 3/1985 | Kuhne | |
| 4,623,536 A | 11/1986 | Winston et al. | |
| 5,045,296 A | 9/1991 | Pfeffer et al. | |
| 5,399,334 A | 3/1995 | Kawakami et al. | |
| 5,407,685 A * | 4/1995 | Malchesky | A01N 25/34 2/16 |
| 5,792,090 A | 8/1998 | Ladin | |
| 6,346,228 B1 | 2/2002 | Chaudhary et al. | |
| 6,552,162 B1 * | 4/2003 | Wang | A61L 15/225 525/162 |
| 6,579,533 B1 * | 6/2003 | Tormala | A61K 9/0024 424/422 |
| 6,582,724 B2 | 6/2003 | Hsu et al. | |
| 6,592,890 B1 | 7/2003 | Green | |
| 6,767,342 B1 | 7/2004 | Cantwell | |
| 6,869,976 B2 | 3/2005 | Royer | |
| 6,939,569 B1 | 9/2005 | Green et al. | |
| 7,014,630 B2 * | 3/2006 | Rosati | A61M 35/00 602/48 |
| 7,160,553 B2 | 1/2007 | Gibbins et al. | |
| 2003/0059471 A1 | 3/2003 | Compton et al. | |
| 2005/0281890 A1 | 12/2005 | San | |
| 2009/0169630 A1 | 7/2009 | Ward et al. | |
| 2009/0202617 A1 | 8/2009 | Ward et al. | |
| 2009/0324668 A1 * | 12/2009 | Kangasniemi | A61K 33/00 424/422 |

(Continued)

FOREIGN PATENT DOCUMENTS

| | | |
|---|---|---|
| DE | 3031485 | 7/1982 |
| DE | 19831798 A1 | 1/2000 |
| EP | 0227955 A2 | 7/1982 |

(Continued)

OTHER PUBLICATIONS

Lentrodt "Hyperbaric Oxygen for Adjuvant Therapy for Chronically Recurrent Mandibular Osteomyelitis in Childhood and Adolescence" American Association of Oral and Maxillofacial Surgeons, 65:186-191 (2007).

(Continued)

*Primary Examiner* — Ali Soroush

(74) *Attorney, Agent, or Firm* — Myers Bigel, P.A.

(57) ABSTRACT

A method of treating hypoxic tissue such as wound tissue comprises contacting a composition to the hypoxic tissue in a hypoxia-treatment effective amount, the composition comprising a biodegradable polymer and an inorganic peroxide incorporated into the polymer.

17 Claims, 7 Drawing Sheets

(56) References Cited

U.S. PATENT DOCUMENTS

2011/0223209 A1    9/2011    Kuijer et al.

FOREIGN PATENT DOCUMENTS

| EP | 0409810 A2 | 1/1991 |
| GB | 2024012 A | 1/1980 |
| JP | 60-261600 | 12/1985 |
| JP | 06107401 | 4/1994 |
| WO | WO 01/49258 A2 | 7/2001 |
| WO | WO 2004/091675 A1 | 10/2004 |
| WO | WO 2006/106049 | 10/2006 |
| WO | WO 2007/134304 A1 | 11/2007 |

OTHER PUBLICATIONS

U.S. Appl. No. 60/800,041, filed May 15, 2006, Ward et al.
Ashikari Y et al. Halogen and chalcogen cation pools stabilized by DMSO. Versatile reagents for alkene difunctionalization. Journal of the American Chemical Society. 2013; 135: 16070-16073.
Canadian Office Action Corresponding to Application No. 2,682,507; dated Jan. 26, 2015; 3 Pages.
Clyne et al., Oxygen tension on the skin of the gaiter area of limbs with venous disease, Aug. 1985, Br. J. Surg., vol. 72., pp. 644-647.
Degim Z et al. An investigation on skin wound healing in mice with a taurine-chitosan gel formulation. Amino Acids. 2002; 22: 187-198.
Dimitrijevich SD et al. Effect of hyperbaric oxygen on human skin cells in culture and in human dermal and skin equivalents. Wound Repair and Regeneration. Jan.-Feb. 1999; 7: 53-64.
International Preliminary Report on Patentability Corresponding to International Applicat No. PCT/US2013/028615; dated Sep. 12, 2014; 6 Pages.
International Search Report, PCT/US2008/004502, dated Aug. 1, 2008.
Radisic M et al. Biomimetic approach to cardiac tissue engineering: oxygen carriers and channeled scaffolds. Tissue EnQineering_. Nov. 8, 2006; 12: 2077-2091.
Radisic M et al. Oxygen gradients correlate with cell density and cell viability in engineered cardiac tissue. Biotechnology and Bioengineering. Feb. 5, 2006; 93(2): 332-343.
Supplementary Search Report, European Patent Application EP 08742617, dated Sep. 20, 2011.
Ward, CL et al. Oxygen Generating Biomaterials Preserve Skeletal Muscle Homeostasis under Hypoxic and Ischemic Conditions. PLOS ONE. Aug. 2013; 8(8): e72485. doi:10.1371/journal.pone.0072485.

* cited by examiner

OXYGEN-GENERATING COMPOSITIONS FOR ENHANCING CELL AND TISSUE SURVIVAL IN VIVO

RELATED APPLICATIONS

This application is a continuation of U.S. application Ser. No. 12/532,520, which is the 35 U.S.C. § 371 national phase application of International Application No. PCT/US2008/004502, filed Apr. 8, 2008, and published in English on Oct. 16, 2008, as International Publication No. WO 2008/124126, and which claims the benefit under 35 U.S.C. § 119(e) of U.S. Provisional Patent Application Ser. No. 60/910,686, filed Apr. 9, 2007, the disclosure of which is incorporated herein by reference in its entirety.

FIELD OF THE INVENTION

The present invention concerns methods and materials for treating hypoxic tissue in vitro and in vivo.

BACKGROUND OF THE INVENTION

Tissue engineering involves assembling cells and their support structures together to restore normal function of diseased or damaged tissue (Langer, R. & Vacanti, J. P. Tissue Engineering. Science 260, 920-926 (1993)). Supplying sufficient oxygen to the engineered tissue is essential for survival and integration of transplanted cells otherwise necrosis occurs. However, limitations of oxygen diffusion has led to a general conception that cell or tissue components may not be implanted in large volumes (Folkman, J. & Hochberg, M. *J Exp Med* 138, 745-53 (1973)).

Numerous efforts have been made to overcome this limitation, which include the use of oxygen rich fluids such as perfluorocarbons and silicone oils (Radisic, M. et al. Biomimetic approach to cardiac tissue engineering: Oxygen carriers and channeled scaffolds. *Tissue Engineering* 12, 2077-2091 (2006); Leung, R., Poncelet, D. & Neufeld, R. J. Enhancement of oxygen transfer rate using microencapsulated silicone oils as oxygen carriers. *Journal of Chemical Technology and Biotechnology* 68, 37-46 (1997)).

Other approaches to maintaining tissue viability attempted include the use of angiogenic factors, such as vascular endothelial growth factors (VEGF) and endothelial cells, and cell-support matrices that permit enhanced diffusion across the entire implant (De Coppi, P. et al. *Tissue Eng* 11, 1034-44 (2005); Kaigler, D. et al., *J Bone Miner Res* 21, 735-44 (2006); Nomi, M. et al., *J. Natl. Cancer Inst.* 93, 266-267 (2001)).

However, the use of oxygen rich fluids and angiogeneic factors have only partially succeeded in achieving survival of a clinically applicable large tissue mass.

SUMMARY OF THE INVENTION

A first aspect of the present invention is a method of treating hypoxic tissue in need thereof, comprising contacting a composition to the hypoxic tissue in a hypoxia-treatment effective amount, the composition comprising a biodegradable polymer and an inorganic peroxide incorporated into the polymer, preferably in solid form (and optionally a radical trap or decomposing catalyst incorporated into and/or onto the polymer in solid form).

In some embodiments the hypoxic tissue is in vivo in a subject in need of the treatment.

In some embodiments, the tissue is wound tissue and the composition is administered in an amount effective to facilitate the healing of the wound tissue.

In some embodiments, the method further comprises the step of concurrently treating the wound tissue with negative pressure wound therapy.

In some embodiments, the tissue is afflicted with an anaerobic infection and the composition is administered in an amount effective to treat the infection.

In some embodiments, the tissue is cancer tissue and the composition is administered in an amount effective to treat the cancer (alone, or in combination with one or more additional therapeutic agents).

In some embodiments, the composition is in the form of a sheet material, and the contacting step is carried out by contacting the sheet material to the tissue. In some embodiments, the composition is in the form of injectable microparticles, and the contacting step is carried out by injecting the microparticles into the tissue. In some embodiments, the composition is in the form of a spray, and the contacting step is carried out by spraying the composition onto the tissue. In some embodiments, the composition is in the form of a surgical or paramedical aid, and the contacting step is carried out by contacting the aid to the tissue.

A second aspect of the invention is a composition comprising, consisting of, or consisting essentially of;

(a) from 50 or 70 to 99 percent by weight of a biodegradable polymer; and (b) from 0.1 to 30 percent by weight of inorganic peroxide incorporated into the polymer in solid form; and (c) optionally from 0.1 to 30 percent by weight of a radical trap or peroxide decomposition catalyst incorporated into the polymer in solid form; and (d) optionally from 0.001 to 5 percent by weight of at least one additional active agent (e.g., antibiotics, growth factors, steroids, antineoplastic agents, etc.). The composition may be in the form of sheet material, injectable microparticles, other shaped articles or scaffolds, etc.

A still further aspect of the invention is, in a method of culturing mammalian tissue in vitro on a solid support or scaffold, the improvement comprising utilizing as the scaffold a composition comprising a biodegradable polymer and an inorganic peroxide incorporated into the polymer in solid form so that oxygenation of the tissue is thereby enhanced.

DETAILED DESCRIPTION OF THE PREFERRED EMBODIMENTS

Figure 1:
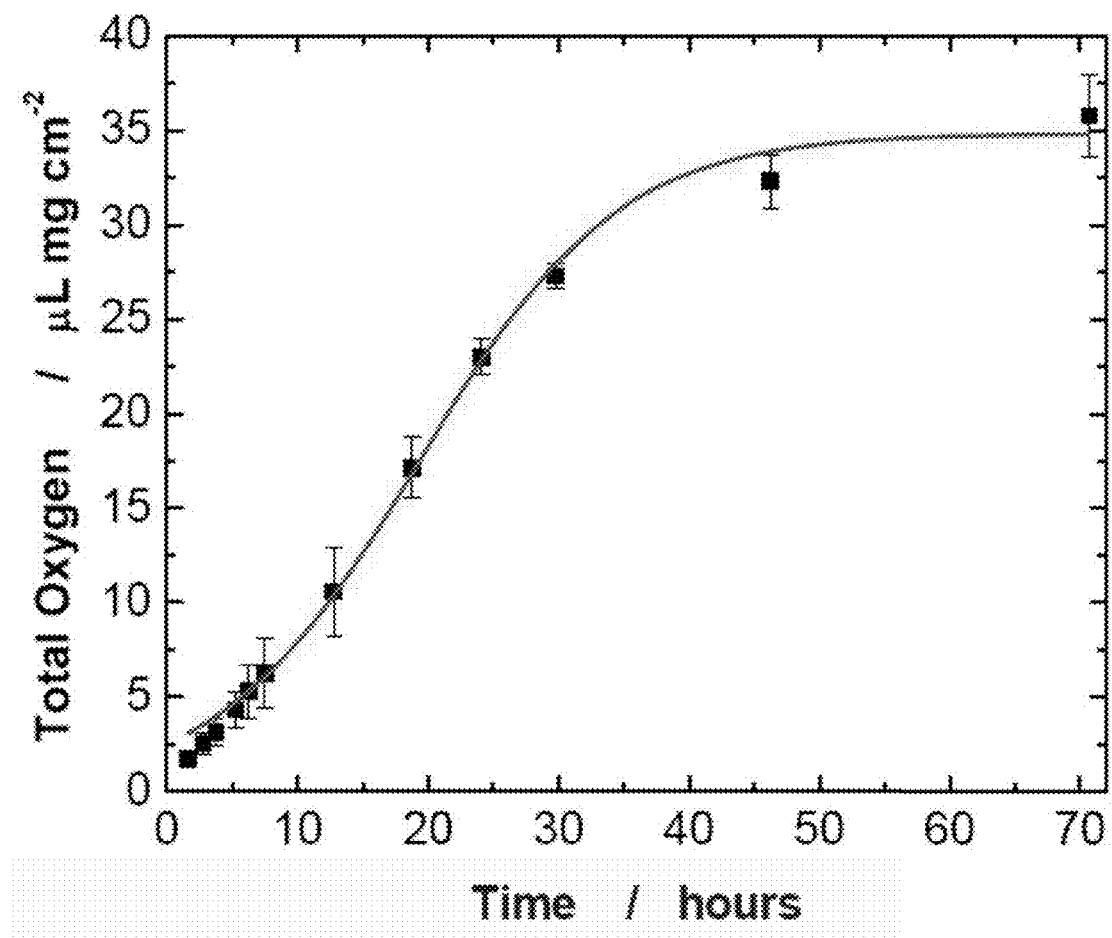
FIG. 1. Oxygen release from POG film, in vitro. In the formulation used the release of oxygen follows a sigmoidal curve with a high rate of oxygen release during the first 24 hours. The control material, PLGA, did not show any oxygen release.

Subjects that can be treated by the methods and compositions of the present invention include both human subjects and animal subjects (including but not limited to other mammalian subjects such as dog, cat, horse, cow, sheep, rabbit, goat, pig, monkey, etc.).

The disclosures of all patent references cited herein are to be incorporated herein by reference in their entirety.

A. Compositions.

Any suitable biodegradable polymer can be used to carry out the present invention, including but not limited to poly(lactide)s, poly(glycolide)s, poly(lactide-coglycolide)s, poly(lactic acid)s, poly(glycolic acid)s, poly(lactic acid-coglycolic acid)s, poly(caprolactone), polycarbonates, polyesteramides, polyanhydrides, poly(amino acid)s, poly(ortho ester)s, polycyanoacrylates, polyamides, polyacetals, poly (ether ester)s, copolymers of poly(ethylene glycol) and poly(ortho ester)s, poly(dioxanone)s, poly(allcylene alkylate)s, biodegradable polyurethanes, as well as blends and copolymers thereof. See, e.g., U.S. Pat. No. 7,097,857; see also U.S. Pat. Nos. 6,991,652 and 6,969,480.

The oxygen-generating active agent is preferably an organic or inorganic peroxide such as urea peroxide, calcium peroxide, and magnesium peroxide, and sodium percarbonate. The oxygen-generating active agent is included in the composition in any suitable amount (e.g., from 0.1 or 1 to 10, 20, or 30 percent by weight, or more). In some embodiments calcium peroxide is preferred as it releases oxygen at a desireable rate in situ. The oxygen-generating active agent can be included in the polymer in solid form, such as in the form of a plurality of solid particles thereof.

In some embodiments a radical trap or peroxide or radical decomposition catalyst is also included in the composition (e.g., in an amount of from 0.1 or 1 to 10, 20 or 30 percent by weight, or more). Suitable examples of radical traps or decomposition catalysts include, but are not limited to, iron (including, but not limited to, iron particles or nanoparticles), enzymes such as catalase, peroxidase; or dehydrogenase (see, e.g., U.S. Pat. No. 7,189,329), compounds such as cyclic salen-metal compounds that have superoxide and/or catalase and/or peroxidase activity (see, e.g., U.S. Pat. No. 7,122,537), etc.). The radical trap or decomposing catalyst may be included in solid form (e.g., solid particulate form) and can be coated on or incorporated in the polymer, or both coated on and incorporated in the polymer.

Sheet materials can be formed of the polymer and the oxygen-generating active agent by any suitable technique, including but not limited to dipping, spraying, casting, extruding, etc.

Injectable microparticles and methods of making the same are known and described in, for example, U.S. Pat. Nos. 7,101,568; 6,455,526; 6,350,464; 5,482,927; 4,542,025; and 4,530,840. Injectable microparticles may be of any suitable size and shape, for example having an average diameter of from 1, 3 or 5 micrometers, up to 300, 500 or 700 micrometers.

In some embodiments (e.g., for use as tissue scaffolds) the compositions are formed into articles such as sheet materials or other formed articles that have a thickness of at least 100 micrometers (approximately the diffusion distance of oxygen in tissue). Irrespective of their shape (e.g., particulate, sheet, or other formed article), the compositions may be solid or porous as desired for the intended use.

The compositions, in the form of sheets, microparticles, or any other suitable form, can be packaged in sterile form in a sterile container for subsequent use.

Injectable microparticles can be provided and injected "dry" or combined with a sterile physiologically acceptable liquid carrier such as physiological saline solution for injection.

In some embodiments, the composition may contain one or more additional active agents (e.g., from 0.0001 or 0.001 to 1, 5 or 10 percent by weight). Examples of such additional active agents include, but are not limited to, chemotherapeutic agents, herbicides, growth inhibitors, anti-fungal agents, anti-bacterial agents, anti-viral agents and anti-parasitic agents, mycoplasma treatments, growth factors, steroids, proteins, nucleic acids, angiogenic factors, anaesthetics, mucopolysaccharides, metals, wound healing agents, growth promoters, indicators of change in the environment, enzymes, nutrients, vitamins, minerals, carbohydrates, fats, fatty acids, nucleosides, nucleotides, amino acids, sera, antibodies and fragments thereof, lectins, immune stimulants, immune suppressors, coagulation factors, neurochemicals, cellular receptors, antigens, adjuvants, radioactive materials, and other agents that effect cells or cellular processes. See, e.g., B. Gibbins et al., US Patent Application Pub. No. 2001/0041188.

"Antibiotic" as used herein may be any suitable antibiotic, including but not limited to Amikacin, Gentamicin, Spectinomycin, Tobramycin, Imipenem, Meropenem, Cefadroxil, Cefazolin, Cephalexin, Cefaclor, Cefotetan, Cefoxitin, Cefprozil, Cefuroxime, Loracarbef, Cefdinir, Cefixime, Cefoperazone, Cefotaxime, Cefpodoxime, Ceftazidime, Ceftibuten, Ceftozoxime, Ceftriaxone, Cefepime, Azithromycin, Clarithromycin, Dirithromycin, Penicillin G, Cloxacillin, Dicloxacillin, Nafcillin, Oxacillin, Amoxicillin, Ampicillin, Mezlocillin, Piperacillin, Nalidixic Acid, Ciprofloxacin, Enoxacin, Lomefloxacin, Norfloxacin, Ofloxacin, Levofloxacin, Sparfloxacin, Alatrofloxacin, Gatifloxacin, Moxifloxacin, Trimethoprim, Sulfisoxazole, Sulfamethoxazole, Doxycycline, Minocycline, Tetracycline, Aztreonam, Chloramphenicol, Clindamycin, Quinupristin, Fosfomycin, Metronidazole, Nitrofurantoin, Rifampin, Trimethoprim, and Vancomycin. See, e.g., U.S. Pat. No. 6,605,609. Antibiotics suitable for use against anaerobic anaerobic bacteria include, but are not limited to, chloramphenicol, metronidazole, imipenem, clindamycin and cefoxitin.

"Growth factor" as used herein basic fibroblast growth factor (bFGF), acidic fibroblast growth factor (aFGF), nerve growth factor (NGF), epidermal growth factor (EGF), insulin-like growth factors 1 and 2, (IGF-1 and IGF-2), platelet derived growth factor (PDGF), tumor angiogenesis factor (TAF), vascular endothelial growth factor (VEGF), corticotropin releasing factor (CRF), transforming growth factors alpha and beta (TGF-alpha and TGF-beta), interleukin-8 (IL-8); granulocyte-macrophage colony stimulating factor (GM-CSF); the interleukins, and the interferons. See, e.g., B. Gibbins et al., US Patent Application Pub. No. 2001/0041188.

"Steroid" as used herein may be any suitable steroid, including but not limited to those described in U.S. Pat. No. 7,157,433

"Antineoplastic agent" as used herein includes, without limitation, platinum-based agents, such as carboplatin and cisplatin; nitrogen mustard alkylating agents; nitrosourea alkylating agents, such as carmustine (BCNU) and other alkylating agents; antimetabolites, such as methotrexate; purine analog antimetabolites; pyrimidine analog antimetabolites, such as fluorouracil (5-FU) and gemcitabine; hormonal antineoplastics, such as goserelin, leuprolide, and tamoxifen; natural antineoplastics, such as taxanes (e.g., docetaxel and paclitaxel), aldesleukin, interleukin-2, etoposide (VP-16), interferon alfa, and tretinoin (ATRA); antibiotic natural antineoplastics, such as bleomycin, dactinomycin, daunorubicin, doxorubicin, and mitomycin; and vinca alkaloid natural antineoplastics, such as vinblastine and vincristine. See, e.g., U.S. Pat. No. 7,101,568.

"Local active agents" or "topical active agents" (i.e., those for local and/or topical administration) as used herein include, but not limited to, those agents set forth above, topical antibiotics and other anti-acne agents, anti-fungal agents, anti-psoriatic agents, antipruritic agents, antihistamines, antineoplastic agents, local anesthetics, anti-inflammatory agents and the like. Suitable topical antibiotic agents include, but are not limited to, antibiotics of the lincomycin family (referring to a class of antibiotic agents originally recovered from *streptomyces lincolnensis*), antibiotics of the tetracycline family (referring to a class of antibiotic agents originally recovered from *streptomyces aureofaciens*), and sulfur-based antibiotics, i.e., sulfonamides. Exemplary antibiotics of the lincomycin family include lincomycin itself (6,8-dideoxy-6-[[(1-methyl-4-propyl-2-pyrrolidinyl)-carbonyl]amino]-1-thio-L-threo-.alpha.-D-galacto-octopyranoside), clindamycin, the 7-deoxy, 7-chloro derivative of lincomycin (i.e., 7-chloro-6,7,8-trideoxy-6-[[(1-methyl-4-propyl-2-pyrrolidinyl)carbonyl]-amino]-1-thio-L-threo-.alpha.-D-galacto-octopyranoside), related compounds as described, for example, in U.S. Pat. Nos. 3,475,407, 3,509,127, 3,544,551 and 3,513,155, and pharmacologically acceptable salts and esters thereof. Exemplary antibiotics of the tetracycline family include tetracycline itself 4-(dimethylamino)-1,4,4.alpha.,5,5.alpha.,6,11,12.alpha.-octahydro-3,6,12, 12.alpha.-pentahydroxy-6-methyl-1,11-dioxo-2-naphthacene-carboxamide), chlortetracycline, oxytetracycline, tetracycline, demeclocycline, rolitetracycline, methacycline and doxycycline and their pharmaceutically acceptable salts and esters, particularly acid addition salts such as the hydrochloride salt. Exemplary sulfur-based antibiotics include, but are not limited to, the sulfonamides sulfacetamide, sulfabenzamide, sulfadiazine, sulfadoxine, sulfamerazine, sulfamethazine, sulfamethizole, sulfamethoxazole, and pharmacologically acceptable salts and esters thereof, e.g., sulfacetamide sodium. Topical anti-acne agents include keratolytics such as salicyclic acid, retinoic acid ("Retin-A"), and organic peroxides, while topical antifungal agents include amphotericin B, benzoic acid, butoconazole, caprylic acid, econazole, fluconazole, itraconazole, ketoconazole, miconazole, nystatin, salicylic acid, and terconazole, and topical antipsoriatic agents include anthralin, azathioprine, calcipotriene, calcitriol, colchicine, cyclosporine, retinoids, and vitamin A. The active agent may also be a topical corticosteroid, and may be one of the lower potency corticosteroids such as hydrocortisone, hydrocortisone-21-monoesters (e.g., hydrocortisone-21-acetate, hydrocortisone-21-butyrate, hydrocortisone-21-propionate, hydrocortisone-21-valerate, etc.), hydrocortisone-17, 21-diesters (e.g., hydrocortisone-17,21-diacetate, hydrocortisone-17-acetate-21-butyrate, hydrocortisone-17,21-dibutyrate, etc.), alclometasone, dexamethasone, flumethasone, prednisolone, or methylprednisolone, or may be a higher potency corticosteroid such as clobetasol propionate, betamethasone benzoate, betamethasone diproprionate, diflorasone diacetate, fluocinonide, mometasone furoate, triamcinolone acetonide, or the like. See, e.g., U.S. Pat. No. 6,582,714.

B. Tissue In Vitro and In Vivo.

Compositions of the invention may be used to treat or oxygenate cells and tissues in vitro by any suitable means, such as by topically applying the composition to the cells (e.g., as a sheet material or as microparticles), growing cells on and/or into the compositions (e.g., compositions in sheet or other solid substrate form), injecting the compositions into cells or tissues being grown in vitro, etc.

Culturing of mammalian tissues (e.g., dog, cat, mouse, monkey, human tissues, etc.) in vitro is known and can be carried out in accordance with known techniques. In general culturing is carried out in a bioreactor, with suitable cells seeded or deposited on a support or scaffold, which scaffold is in turn placed in a suitable growth or culture media. See, e.g., U.S. Pat. Nos. 4,940,853; 6,592,623; 6,645,759; 6,645,759; etc. Examples of suitable tissues for culturing include, but are not limited to, bone tissue, skin tissue (e.g., dermal tissue), skeletal muscle, cardiac muscle, vascular (e.g., blood vessel) tissue, and other tissues that are comprised of oxygen-sensitive cells.

In still further embodiments, the compositions as described above can be implanted in vivo as a tissue scaffold in a suitable subject, particularly in regions where circulation might otherwise be impaired.

C. Wound Treatment.

In some embodiments the region of interest or the tissue being treated is a wound site or a region adjacent the wound site in a patient or subject afflicted with that wound.

"Wound" as used herein includes any type of accidental or deliberate (e.g., surgical) tissue trauma, including but not limited to incisions, lacerations, ulcers, abrasions, burns, crush injuries, amputations, punctures, and combinations thereof.

"Wound tissue" is tissue the health of which is deleteriously affected by a wound (e.g., disrupted circulation as in a skin flap, crush injury, etc.).

In some embodiments the wound or wound tissue is also infected or afflicted with an anaerobic infection as described further herein.

In one embodiment of the invention, the compositions are administered to wounds of subjects that are concurrently undergoing treatment with negative pressure wound therapy. For example, in some embodiments, a composition of the invention in the form of a sheet material (which may optionally contain perforations) is applied to a wound or wound tissue before or shortly before a negative pressure chamber is applied over the wound tissue and negative pressure is applied, so that oxygen is administered from the composition to the afflicted tissue during the negative pressure wound therapy. In this embodiment, the sheet material may optionally serve as the "interface" or "dressing" in the negative pressure wound therapy system. In other embodiments, the composition in the form of injectable microparticles is topically applied to the wound tissue or injected into the wound tissue (e.g. injected below the surface of the wound, under the wound, into regions immediately adjacent the wound to facilitate oxygen transfer into afflicted tissue) before or shortly before a negative pressure chamber is applied over the wound tissue and negative pressure is applied thereto, so that oxygen is administered from the composition to the afflicted tissue during the negative pressure wound therapy. Negative pressure wound therapy is known and describes techniques in which wound healing is facilitated by the application of a vacuum, or negative pressure, to the wound. See, e.g., U.S. Pat. No. 5,645,081 The specific modality of implementation is not critical and any of a variety of techniques can be employed, including but not limited to those described in U.S. Pat. Nos. 7,004,915; 6,951,553; 6,855,135; 6,800,074; 6,695,823; and 6,458,109.

When used to treat wounds, the composition may optionally contain one or more additional local or topical active agents to facilitate growth or treat infection (e.g. an antibiotic), treat pain (e.g., an analgesic), treat inflammation (e.g., an antiinflammatory agent such as a nonsteroidal antiinflammatory agent) as described above.

D. Surgical Aids, Paramedic Aids, and Sprays.

Surgical and paramedic aids can be produced from the materials of the invention. Such aids generally comprise comprise a biodegradable polymer and an inorganic peroxide incorporated into said polymer in solid form, as described above. The aid can be in any suitable form, such as a sponge, packing, wound dressing (gauze, adhesive bandage, etc.,), suture, etc. A support material for the biodegradable polymer can be provided if desired, with the polymer contacted to the support material in the form of a sheet, powder, particles, etc. The aid can be packaged in sterile form in a suitable container, or provided in non-sterile form for sterilization by the user.

For some applications the compositions can be provided as spray compositions, the spray compositions comprising a carrier (e.g., an aqueous or non-aqueous carrier), a biodegradable polymer, and an inorganic peroxide in solid form, as described above. The polymer can be solubilized or dispersed in the carrier (that is, the spray compositions can be in the form of solutions, suspensions, dispersions, microdispersions, emulsions, etc.). The spray compositions can be provided in a suitable spray applicator such as a pump-type spray applicator, or can be packaged in an aerosol container with a suitable propellant (e.g., HFA-134a, HFA-227ea, carbon dioxide) to provide an aerosol spray device containing an aerosol spray composition. The spray compositions may advantageously include additional active agents, all as described above. Such spray compositions can be formulated in accordance with known techniques or variatious thereof that will be apparent to those skilled in the art. See, e.g U.S. Pat. Nos. 7,182,277; 7,163,672; 7,101,535; 7,090,831; 7,074,388; 6,218,353; etc.

E. Anaerobic Infections.

The compositions of the invention may be used to treat anaerobic infections in any tissue so infected, for example in a subject afflicted with such an infection. Anaerobic infections may be caused by any of a variety of anaerobic bacteria, including but not limited to *Bacteroides* species (e.g., *Bacteroides fragilis*), *Peptostreptococcus*, and *Clostridium* species (e.g., *Clostridium perfringens*).

Examples of anaerobic infections include, but are not limited to, gas gangrene, clostridial myonecrosis, necrotizing infections such as necrotizing fascitis, etc. Particular examples include anaerobic infections of the mouth, head, and neck (e.g. infections in root canals, gums (gingivitis), jaw, tonsils, throat, sinuses, ears, etc.); anaerobic infections of the lung (e.g., as in pneumonia, lung abscesses, infection of the lining of the lung (empyema), and dilated lung bronchi (bronchiectasis)); anaerobic infections of the abdominal cavity, such as intraabdominal abscess formation, peritonitis, and appendicitis; anaerobic infections of the female genital tract (e.g., pelvic abscesses, pelvic inflammatory disease, inflammation of the uterine lining (endometritis), and pelvic infections following abortion, childbirth, and surgery); anaerobic infections of skin and soft tissue (e.g., diabetic skin ulcers, gangrene, destructive infection of the deep skin and tissues (necrotizing fascitis), and bite wound infections); anaerobic infections of the central nervous system (e.g., cause brain and spinal cord abscesses); bacteremia; etc.

The route of administration will depend upon the particular type of infection and the tissue infected. In some embodiments a sheet material of the composition may be applied in like manner as described in connection with wounds above. In other embodiments injectable microparticles of the composition may be injected as described in connection with wounds above. Multiple routes of administration (e.g., both topical and injection) may be used. Surgical removal of damaged tissue and/or drainage of adversely affected areas (e.g., by negative pressure wound treatment or any other means) may also be used. Multiple administrations may be desired. The compositions may have an additional active agent such as one or more antibiotics incorporated therein, as also described above.

F. Tumor Treatment.

In some embodiments, the compositions of the invention can be used to treat a tumor or cancer in a subject in need thereof by administering the compositions to a subject in need thereof. Administration may be carried out by any technique that brings the compositions into contact with tumor cells, including but not limited to injecting the composition in microparticle form into the tumor, or into a region containing or adjacent the tumor. Tumors or cancers that can be treated include but are not limited to lung, colon, liver, prostate, breast, ovarian, skin, and pancreatic cancer.

The present invention is explained in greater detail in the non-limiting examples set forth in the experimental section below.

Experimental

Here we show that implantable oxygen releasing biomaterials can provide a sustained release of oxygen to cells and tissues resulting in prolonged tissue survival and decreased necrosis. Both visibly and histologically, significant decreases in necrosis were observed for least two days after implantation of the oxygenating biomaterial in mice. Our results show that oxygen producing biomaterials can release oxygen into hypoxic tissues resulting in a delayed onset of necrosis. These findings are also applicable to treating cancer, since hypoxia has been shown to promote the aggressiveness of cancer cells (Hockel, M. & Vaupel, P. *J.*

*Natl. Cancer Inst.* 93, 266-267 (2001)). In addition, this technology is also be useful for various wound healing and reconstructive applications including plastic surgery with flaps and treatment of anaerobic infections (Jonsson, K. et al., *Annals of Surgery* 214, 605-613 (1991); Bowler, P. G. et al., *Clinical Microbiology Reviews* 14, 244 (2001)).

First, we prepared a polymeric oxygen generating (POG) film by dispersing sodium percarbonate (SPO) into poly (lactide-co-glycolide) (PLGA). Sodium percarbonate is an adduct of hydrogen peroxide and sodium bicarbonate which spontaneously decomposes upon contact with water to produce oxygen. When the POG films are placed in a moist environment at 37° C., oxygen production was observed over a 24 hour period. (FIG. 1). As expected, no oxygen release was detected from the control films of PLGA. To study how oxygen generating biomaterials can affect critically/marginal perfused tissues in vivo we used the skin flap model in mice. This model is well accepted as serves as a standard for research on ischemic tissue survival (Buemi, M. et al., *Shock* 22, 169-173 (2004); Giunta, R. E. et al., *J. Gene Med* 7, 297-306 (2005); Gould, L. J. et al., *Wound Repair Regen.* 13, 576-582 (2005)). 11-13 We analyzed the adjacent tissue flaps on tissue, cellular and biochemical levels.

After generating the rectangular dorsal skin flaps, an oxygen producing film was placed in the subcutaneous space in all animals, and the surgical wound was closed. PLGA films containing no sodium percarbonate were used as controls. The size of tissue necrosis was measured at 2, 3 and 7 days. The analysis of graft necrosis shows a significant benefit for the SPO group in the early time points with $p=0.001$ at 2 days and $p=0.025$ at 3 days, respectively.

Figure 2:
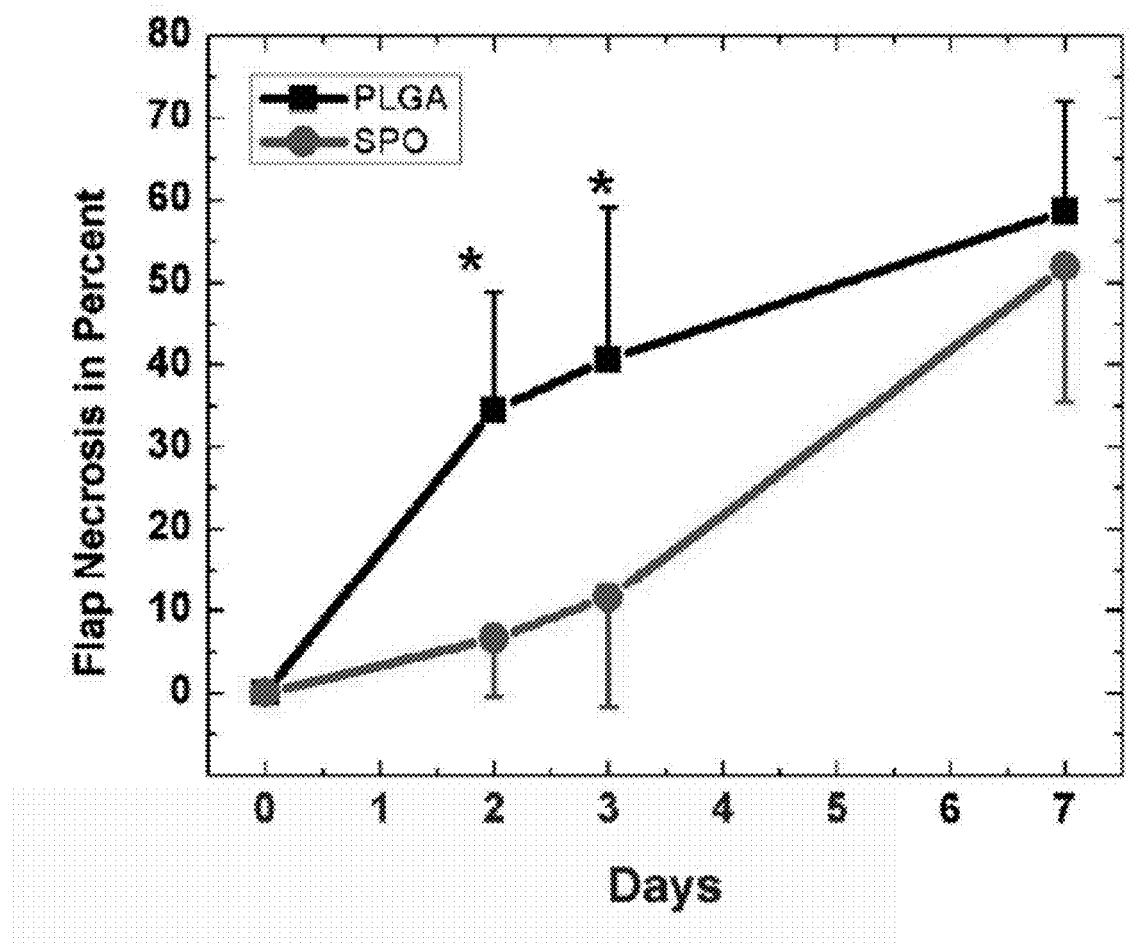
FIG. 2: Flap Necrosis. Graph expressing the necrosis in percent of total flap size. At early time points, 2 and 3 days, the SPO group showed a significant better flap survival with less necrosis, when compared to the control group. However, after 7 days the area of necrosis was similar in both groups.

After 7 days however, the size of tissue necrosis were comparable between the two groups ($p=0.74$). (FIG. 2) The prevention of necrosis by the oxygen releasing biomaterial is a key finding on this study and might indicate that the early supplementation with oxygen was able to delay tissue death. Characterization at a cellular level involved histological examination of tissue sections at 3 and 7 days. Tissue sections were stained with hematoxyin and eosin to explore the extent of tissue necrosis. Overall, there was a clear survival benefit for the POG group with better preservation of general tissue architecture, epidermis height, hair follicles and sebaceous glands. In the early time point, the control group had already lost much of the height of the stratified layer and the dermis. Hair follicle and the glands were less defined when compared to the POG group. However, at 3 days the general tissue architecture was conserved in both groups including, clearly defined epidermis and dermis separated by basal cells and the basilar membrane. In the control group this picture changed drastically at 7 days with disruption of tissue architecture and vague transitions between the layers and an eosin positive mass replacing the dermis. The loss of dermal papilla, sebaceous glands and hair follicle defined a more advanced stage of necrosis. The POG group showed a slower progression with remaining defined layers and intact hair follicles. Both groups showed a mixed cellular infiltration starting from the flap edge, with a tendency for higher cellular content in the dermis of the POG group.

Figure 3:
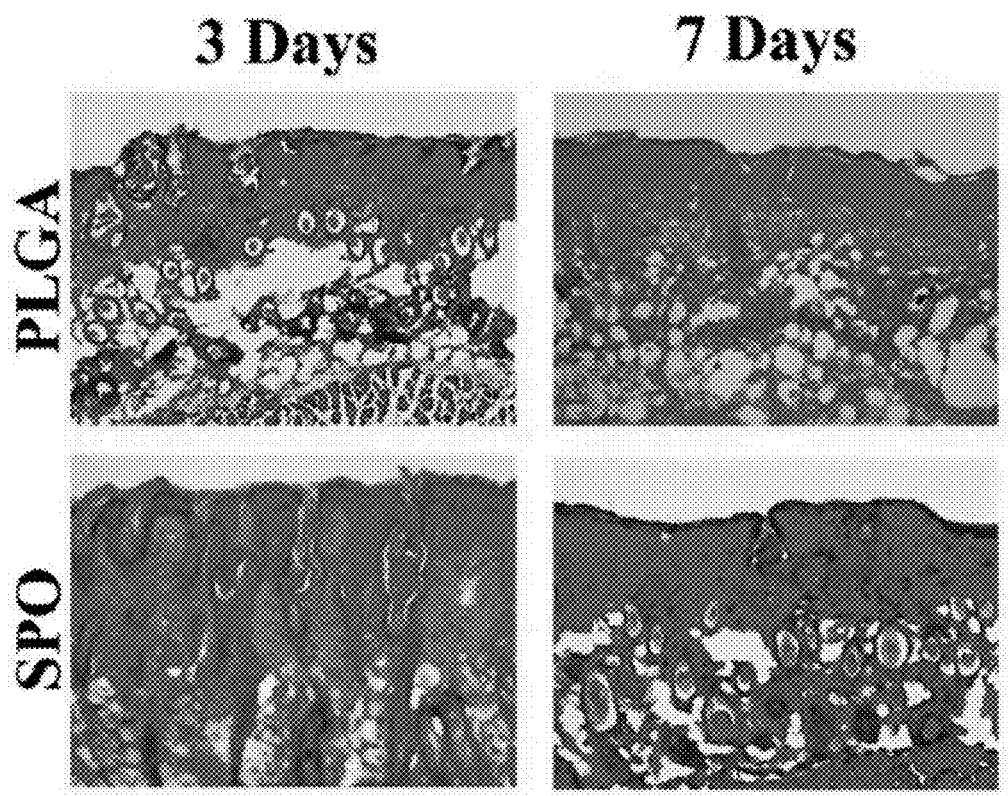
FIG. 3: Histological Analysis, 100×: Hematoxylin and Eosin stains of the skin flaps harvested at 3 and 7 days showed delayed necrosis in the SPO group with better conservation of tissue architecture, epidermis height, hair follicles and sebaceous glands. Differences were more prominent at the 7 day time point.

To compare the induction of apoptosis in the flaps of the two groups, we performed a TUNEL stain (FIG. 3). We found significantly lower amounts of apoptosis positive cells in the dermis of the POG group at 3 days ($p=0.030$). Due to the more advanced stage of tissue degradation with disruption of the nuclear envelope at 7 days the TUNEL stain was only able to show poorly defined DNA smears. In summary, the histological findings and significant lower level of apoptosis indicate a delayed onset of necrosis in the group with the oxygen releasing biomaterial.

Figure 4:
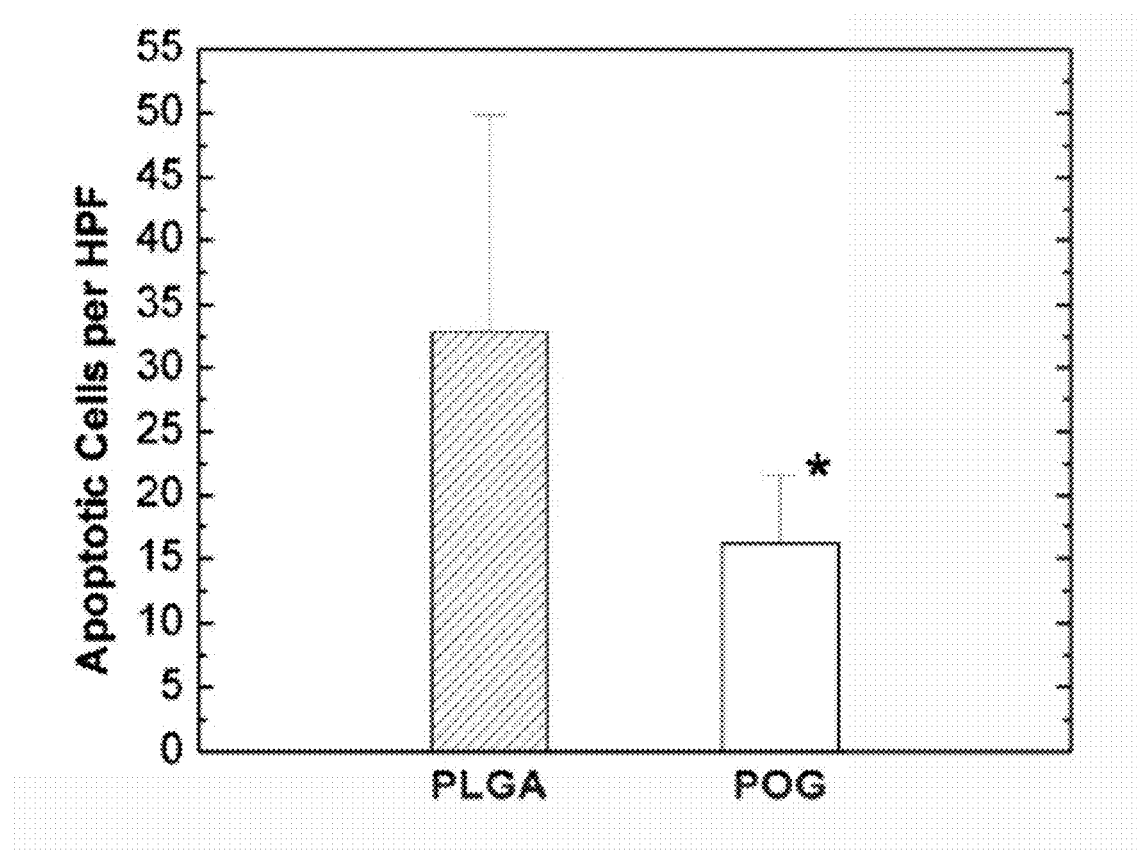
FIG. 4: Evaluation of Apoptosis after 3 days: a, representative sections of dermis showing apoptosis positive cells with brown nuclei (nuclei counterstained with methyl green). b, A significant higher number of apoptotic cells were found in the dermis of the control (PLGA) group when compared with the treatment group (SPO). The oxygen generating biomaterial was able to prevent or delay the induction of apoptosis in the skin flap.

Apoptosis was evaluated in flap tissue treated by the compositions of the invention after three days (FIG. 4). FIG. 4a provides representative sections of dermis showing apoptosis positive cells with brown nuclei (nuclei counterstained with methyl green). As shown in FIG. 4b, a significantly higher number of apoptotic cells were found in the dermis of the control (PLGA) group when compared with the treatment group (SPO). The oxygen generating biomaterial was able to prevent or delay the induction of apoptosis in the skin flap.

Figure 5:
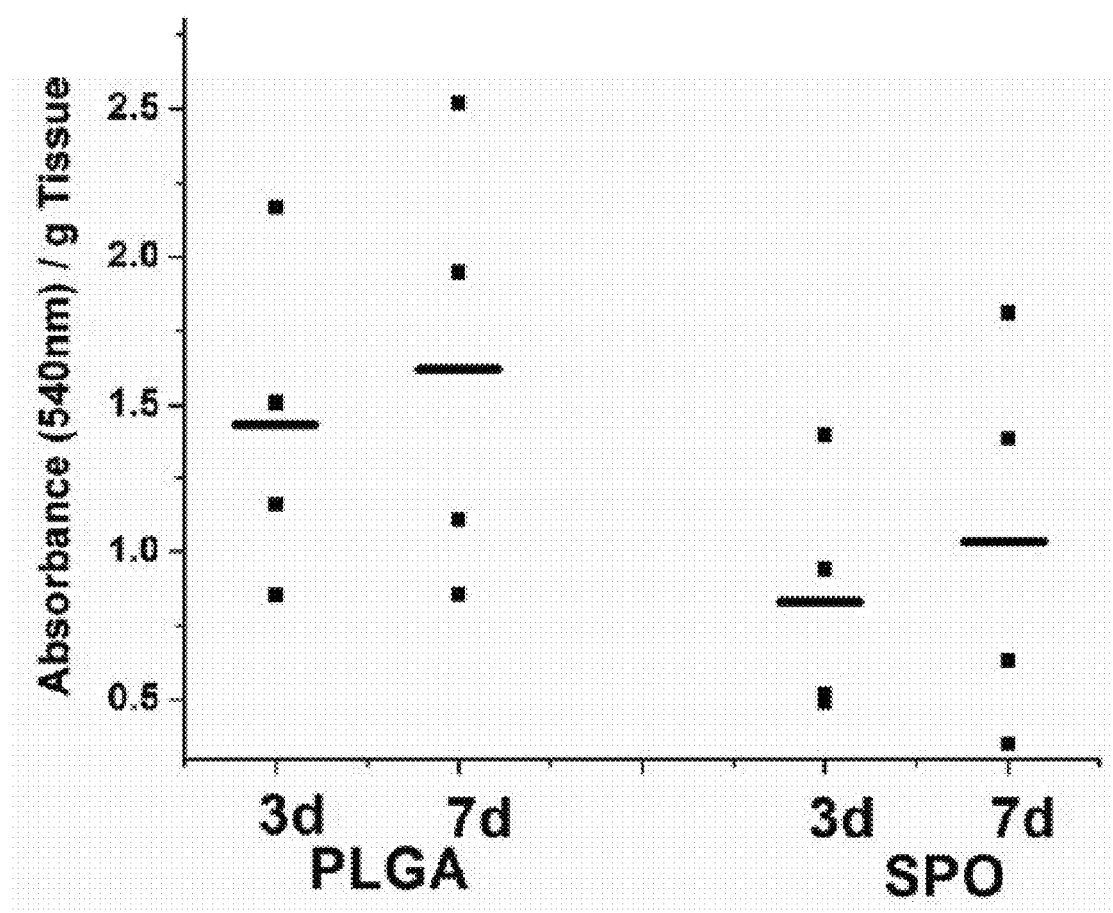
FIG. 5: Tissue Lactate Levels: Graph presenting the flap tissue lactate levels corrected for tissue weight. Individual dots are presenting each animal and bars indicate the average of the group. High level of lactate is an indication of low oxidative metabolism due to low oxygen tension in tissues. The SPO group shows better results with lower levels of lactate, when compared to PLGA only.

Additional investigations at the biochemical level were conducted by measuring the lactate concentration in the flap tissue. Higher concentrations of lactate are related to various medical conditions inducing anaerobe metabolism and, therefore, a reliable measure for anaerobic metabolism do to poor vascularization. We found that the tissue flaps with underlying oxygen producing biomaterial had lower lactate levels when compared to the control group. (FIG. 5) The difference was more prominent at the early time point with the POG group having 57% lactate of the control group. The lactate levels in both groups increased at the seven day time point. The anticipated increase after seven days is countered by the reduction of living cells in the tissue. The lower level of lactate in the POG group is a further indication that the oxygen releasing biomaterial is able to support cellular survival.

Figure 6:
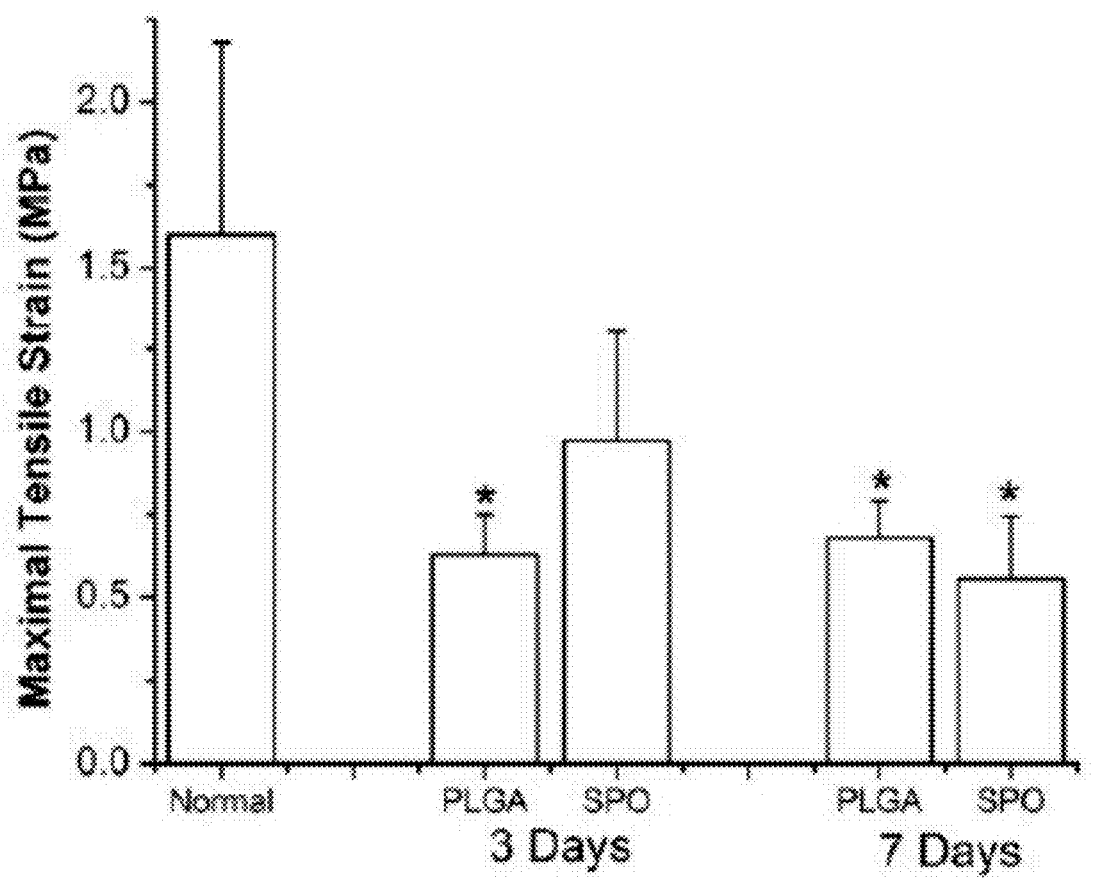
FIG. 6: Biomechanical Testing. Graph showing the maximal tensile strain at break in MPa. In average, the SPO group showed a higher maximal tensile strain at the 3 day time point with no statistical difference when compared to normal skin. This indicates that the SPO was able to delay the breakdown of proteins in the extracellular matrix of the dermis. At the 7 day the strains of the two groups were comparable.

To further investigate the impact of the oxygen releasing biomaterial on tissue integrity, we measured wound breaking strengths. (FIG. 6) At time of harvest longitudinal tissue specimens were cut form the skin flap and pulled to failure. In the early time point skin samples from the control had already lost significant strength ($p=0.028$) when compared to normal skin. The decrease of strength in the POG group was not significant ($p=0.130$). However, after 7 days both samples were comparable and showed significant loss of strength with $p=0.008$ for the PLGA group and $p=-0.004$ for the POG group, respectively. Biomechanical testing was able to show a benefit in tissue integrity for the POG group in the early time points. Since degradation of extracellular matrix proteins through hydrolysis and enzymatic degradation is common during tissue death the higher tissue strength in the POG group indicates a delayed tissue necrosis.

Figure 7:
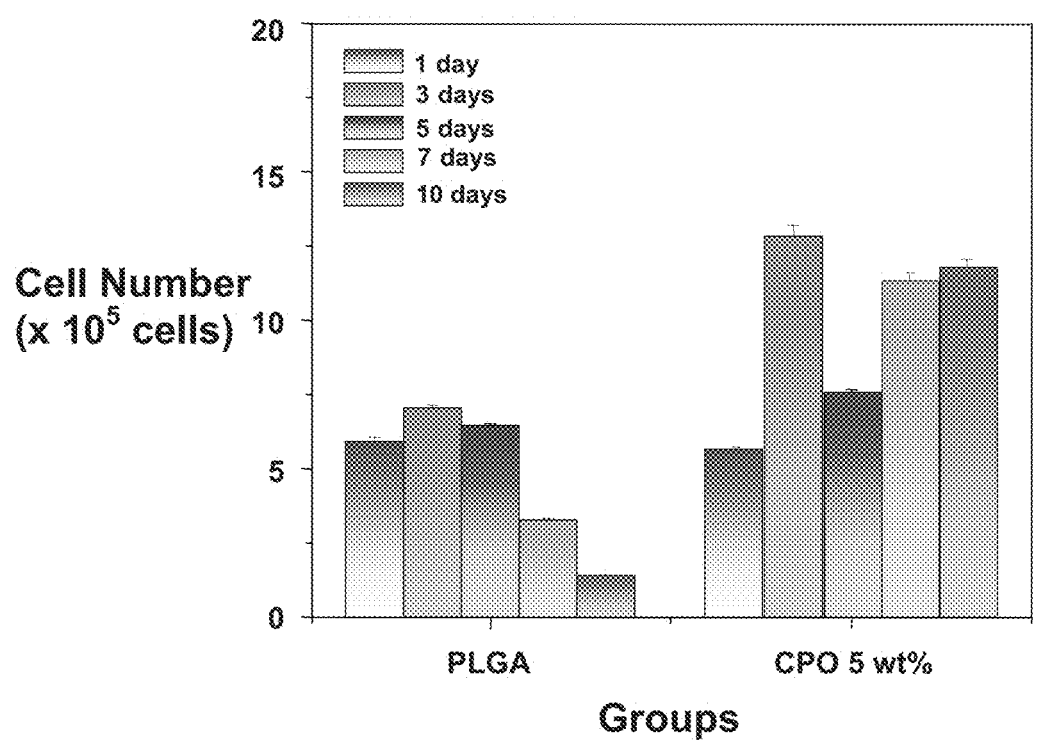
FIG. 7: Enhanced cell viability is observed when 3T3 cells incorporated into an approximately 1 cm cube PLGA scaffold containing calcium peroxide (CPO) are incubated under extend hypoxic (<1% oxygen) conditions. The control contains no oxygen producing materials.

As shown in FIG. 7, enhanced cell viability is observed when 3T3 cells incorporated into an approximately 1 cm cube PLGA scaffold containing calcium peroxide (CPO) are incubated under extended hypoxic (<1% oxygen) conditions. The control contains no oxygen producing materials. Note in particular that ten days of data are shown.

Methods

Production of Polymeric Oxygen Generating Films.

The Poly(D,L-lactide-coglycolide) (PLGA 50:50, i.v. 0.89 dl/g in HFIP at 30° C., Lactel Absorbable Polymers, Pelham Ala.) films incorporating sodium percarbonate (SPO, Geel, Belgium) or calcium peroxide (CPO) were fabricated using a solvent casting process from mixtures of PLGA and SPO. Briefly, PLGA was dissolved in methylene chloride (5% w/v) and SPO was pulverized by freezer-mill (SPEX 6700, Mutchen, N.J.). PLGA solution and SPO were thoroughly mixed using a vortex. Films were cast from PLGA solution on Pyrex glass dish (Φ100) containing SPO in specified concentrations. In order to prevent the formation of voids within the polymer films a glass cover was put on the moulds to provide slow solvent evaporation. After 48 hrs of solvent evaporation, the films were dried for 72 hrs in a drying chamber under vacuum condition at room temperature. PLGA film without SPO was used as a control, and was fabricated using the same method. All other chemicals of analytical grade were purchased from Sigma (St. Louis, Mo.). Oxygen release was measured by recording the displaced volume of water displaced with the collected oxygen gas generated.

Animal Model:

16 nude mice (Nude-nude, Charles River Laboratories Inc. Wilmington, Mass.) were randomized into 2 groups. Group 1 received the oxygen releasing biomaterial (SPO) while Group 2 served as the control group and received the PLGA only biomaterial (PLGA). Four animals of each group were sacrificed on day 3 and day 7. All procedures were performed in accordance with the Animal care and use committee. We used the established skin flap model in mice to produce critically vascularized skin flaps. All surgeries were performed under general anesthesia using isoflurane 2%. Skin flaps 30×10 mm in size were created on the back. The u-shaped flap reduced the intact vascularity to the 1 cm wide base. In both groups a 20×10 mm large biomaterial was placed subcutaneous between muscle and skin layer. The surgical wound was then closed using absorbable suture material in a running fashion. All animals survived the surgeries without complications. During the first 24 h the mice received routine analgesic injection with buprenorphine 0.1 mg/kg 3 times per day. The animals were allowed free access to food and water and housed in a 12 hour day/night cycle. At time of sacrifice the animals were euthanized by $CO_2$. For consistency tissue samples for all the individual tests were taken in a standard fashion.

Assessment of Graft Necrosis.

At day 2, 3 and 7 all animals were anesthetized by isoflurane 2% and photographed under standard lighting. The necrosis was clearly visible with a change in skin color towards brown/black. The flap necrosis was measured by image analysis (Image J, NIH) and expressed in percent of total flap size.

Histology.

Skin samples harvested at 3 and 7 days were embedded in Tissue-Tek® O.C.T. Compound 4583 (Sakura®), frozen in liquid nitrogen and sectioned into 6-8 μm slices using a cryostat (CM 1850 Cryotsat, Leica, Bannockburn, Ill.). Tissue samples of each animal were stained with hematoxylin and eosin using standard protocols. Histology was used to assess the level of inflammation, remaining tissue architecture and necrosis. Further, TUNEL staining (TACS TdT Kit, R&D Systems, Minneapolis, Minn.) was performed according to the manufactures guidelines to investigate the level of induced apoptosis within the epidermis of the skin flaps. Images were taken using a Zeiss Axio Imager M1 Microscope (Carl Zeiss, Thornwood, N.Y.). Image analysis was performed using Image J (NIH) Image analysis Software. Number of apoptotic cells per high power field (400×) was counted and compared between the groups.

Lactate Assay.

Tissue samples were stored at −80° C. and homogenized using cryo grinding. The powder was weighed and the tissue particles further dissolved in cold 3M $HClO_4$ (0.15 ml per vial) of for 20 Minutes. All tubes were handled in an ice/salt bath at −8° C. Following a centrifugation at 11,500 RPM for 10 minutes at 4° C. the supernatant was collected and tissue L-lactate determined spectrophotometrically using a commercially available kit (Lactate Assay Kit, BioVision Research, Mountain View, Calif.). Briefly, samples were transferred to a 96 well dish containing enzyme and reaction buffer. After 30 minutes at room temperature the colorimetric change was measured by a spectrophotometrically at 540 nm.

Biomechanical Testing.

Rectangular longitudinal tissue strips (30 mm×5 mm) were used to evaluate the would-braking strength. Tensile tests (Instron model 5544, Issaquah, Wash., USA) were performed by elongating the tissue strips longitudinally at a speed of 0.05 mm/second with a preload of 0.2 N until failure. The grip-to-grip spacing was 2 cm. All specimens were tested at room temperature and kept moist. The maximum tensile strain (MPa) was determined.

Statistics.

All presented data is expressed as averages and the corresponding standard deviations. For statistical analysis we used SPSS v11 (SPSS Inc). Differences between the two groups were analyzed by 2 tailed independent samples T test. For the analysis of the biomechanical properties we used one-way analysis of variance (ANOVA) followed by a Bonferroni test for multiple comparisons. A p value of less then 0.05 was considered significant.

The foregoing is illustrative of the present invention, and is not to be construed as limiting thereof. The invention is defined by the following claims, with equivalents of the claims to be included therein.

That which is claimed is:

1. A method of treating hypoxic tissue in need thereof, comprising:
   contacting a composition to said hypoxic tissue in a hypoxia-treatment effective amount,
   wherein said composition comprises a biodegradable polymeric film and an inorganic peroxide incorporated into said polymeric film,
   wherein said inorganic peroxide comprises a plurality of solid inorganic peroxide particles, and
   wherein said hypoxic tissue is wound tissue, tissue afflicted with an anaerobic infection or cancer tissue.

2. The method of claim 1, wherein said hypoxic tissue is in vivo in a subject in need of said treatment.

3. The method of claim 1, wherein said tissue is wound tissue and said composition is administered in an amount effective to facilitate the healing of said wound tissue.

4. The method of claim 2, further comprising the step of concurrently treating said wound tissue with negative pressure wound therapy.

5. The method of claim 1, wherein said tissue is afflicted with an anaerobic infection and said composition is administered in an amount effective to treat said infection.

6. The method of claim 1, wherein said tissue is cancer tissue and said composition is administered in an amount effective to treat said cancer.

7. The method of claim 1, wherein said composition is in the form of a sheet material, and said contacting step is carried out by contacting said sheet material to said tissue.

8. The method of claim 1, wherein said composition is in the form of a surgical or paramedical aid, and said contacting step is carried out by contacting said aid to said tissue.

9. The method of claim 1, wherein said biodegradable polymeric film comprises a polymer selected from the group consisting of polylactide, polyglycolide, poly lactide-glycolide copolymers, and alginate.

10. The method of claim 1, wherein said peroxide is calcium peroxide.

11. The method of claim 1, wherein said peroxide is sodium percarbonate.

12. The method of claim 1, wherein said composition comprises:
(a) from 70 to 99 percent by weight of the biodegradable polymeric film; and
(b) from 1 to 30 percent by weight of the inorganic peroxide incorporated into said polymeric film;
(c) optionally from 0.1 to 30 percent by weight of a radical trap or peroxide decomposition catalyst incorporated into the polymeric film in solid form; and
(d) optionally from 0.001 to 5 percent by weight of at least one additional active agent.

13. The method of claim 12, wherein said composition is in the form of a sheet material.

14. The method of claim 12, wherein said biodegradable polymeric film comprises a polymer selected from the group consisting of polylactide, polyglycolide, poly lactide-glycolide copolymers, and alginate.

15. The method of claim 12, wherein said at least one additional active agent is selected from the group consisting of antibiotics, growth factors, steroids, and antineoplastic agents.

16. The method of claim 12, wherein said peroxide is calcium peroxide.

17. The method claim 12, wherein said peroxide is sodium percarbonate.

* * * * *

UNITED STATES PATENT AND TRADEMARK OFFICE
CERTIFICATE OF CORRECTION

PATENT NO.         : 10,493,041 B2                                              Page 1 of 1
APPLICATION NO.    : 16/142480
DATED              : December 3, 2019
INVENTOR(S)        : Harrison et al.

It is certified that error appears in the above-identified patent and that said Letters Patent is hereby corrected as shown below:

On the Title Page

Item (72) Inventors:
Please correct "Benjamin C. Harrison" to read -- Benjamin S. Harrison --

Item (56) References Cited, OTHER PUBLICATIONS, Page 2, Column 1, Ashikari Yet al. cite:
Please correct "Ashikari Yet al." to read -- Ashikari Y et al. --

In the Specification

Column 10, Line 38:
Please correct "p=-0.004" to read -- p=0.004 --

Signed and Sealed this
Twelfth Day of May, 2020

Andrei Iancu
*Director of the United States Patent and Trademark Office*